United States Patent
McElhanon et al.

(10) Patent No.: US 7,449,579 B1
(45) Date of Patent: Nov. 11, 2008

(54) DETECTION OF ELECTROPHILIC AND NUCLEOPHILIC CHEMICAL AGENTS

(75) Inventors: James R. McElhanon, Manteca, CA (US); Timothy J. Shepodd, Livermore, CA (US)

(73) Assignee: Sandia Corporation, Livermore, CA (US)

( * ) Notice: Subject to any disclaimer, the term of this patent is extended or adjusted under 35 U.S.C. 154(b) by 22 days.

(21) Appl. No.: 11/416,667

(22) Filed: May 2, 2006

(51) Int. Cl.
*C07D 491/00* (2006.01)

(52) U.S. Cl. ........................................................ 546/90
(58) Field of Classification Search ........................ None
See application file for complete search history.

(56) References Cited

U.S. PATENT DOCUMENTS

| | | | |
|---|---|---|---|
| 5,019,350 A | 5/1991 | Rhum et al. | |
| 5,075,215 A | 12/1991 | Dreyer | |
| 5,132,206 A | 7/1992 | Dreyer | |
| 5,354,825 A | 10/1994 | Klainer et al. | |
| 5,945,343 A | 8/1999 | Munkholm | |
| 6,080,516 A | 6/2000 | Devlin et al. | |
| 6,344,654 B1 | 2/2002 | Lesko | |
| 6,521,185 B1 | 2/2003 | Groger et al. | |
| 6,623,973 B2 | 9/2003 | Levitsky et al. | |
| 6,821,738 B2 | 11/2004 | Harmon | |
| 2005/0147534 A1* | 7/2005 | Swager et al. | ............ 422/82.05 |

OTHER PUBLICATIONS

Le et al., Journal of Organic Chemistry, 2004, vol. 69, pp. 2768-2772.*
Pavelk, A. S, The Fluorescense Properties of Protoberbine and Tetrahydroprotoberbine Alkaloids, Coll. Czech. Chem. Commun., 1976, 3157, 3169, 41.

* cited by examiner

*Primary Examiner*—Zinna N Davis
(74) *Attorney, Agent, or Firm*—Donald A. Nissen

(57) ABSTRACT

A "real time" method for detecting electrophilic and nucleophilic species generally by employing tunable, precursor sensor materials that mimic the physiological interaction of these agents to form highly florescent berberine-type alkaloids that can be easily and rapidly detected. These novel precursor sensor materials can be tuned for reaction with both electrophilic (chemical species, toxins) and nucleophilic (proteins and other biological molecules) species.

1 Claim, 2 Drawing Sheets

DETECTION OF ELECTROPHILIC AND NUCLEOPHILIC CHEMICAL AGENTS

STATEMENT OF GOVERNMENT INTEREST

This invention was made with Government support under contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

CROSS-REFERENCE TO RELATED APPLICATIONS

Not applicable.

FIELD OF THE INVENTION

This invention is directed to a method for the detection of electrophilic and nucleophilic species generally and, in particular, to the detection of chemical and biological warfare agents by reaction with precursor sensor materials to produce readily detectable fluorescent berberine-based alkaloids.

BACKGROUND OF THE INVENTION

Rapid and sensitive detection of chemical warfare and biological agents have been an area of growing interest and importance. There are many current approaches toward chemical warfare agent (CWA) detection such as ion mobility spectroscopy (Cottingham, K. *Anal. Chem.* Oct. 1, 2003, 435A-439A), surface acoustic wave (Williams D.; Pappas G. *Field Anal. Chem. Technol.* 1999, 3, 45-53), microcantilever (Yang Y.; Ji H-F.; Thundat T. *J. Amer. Chem. Soc.* 2003, 125, 1124-1125) and interferometric devices (Sohn H.; Letant S.; Sailor M. J.; Trogler W. C. *J. Amer. Chem. Soc.* 2000, 122, 5399-5400). While some of these methods show CWA simulant detection at low concentrations, specificity and discrimination among chemical threat agents is still lacking. Swager (Zhang S-W.; Swager T. M. *J. Amer. Chem. Soc.* 2003, 125, 3420-3421) has disclosed a novel fluorescent chemical detection method that yielded fluorescent species upon reaction with CWA simulants. However, Swager's chemical sensors do not allow for chemical modification amenable to a broad range of analytical platforms and suffer from low Stokes shifts (65 nm) with significant overlap of exciting light absorption and fluorescent emission. This effect results in low detection sensitivity to CWA simulants. Slow kinetics also limits sensitivity. Furthermore, it is important that the detection method or materials used allow for integration into multiple analytical platforms Moreover, long-wavelength fluorogenic chemical sensors that are reactively activated by biological agents do not exist. Fluorescent markers (e.g. green fluorescent protein and derivatives) currently used in cell biology are costly and suffer from background fluorescence from unreacted probes in experiments designed to detect molecular interactions

SUMMARY OF THE INVENTION

The instant invention takes advantage of the observation that certain materials, hereinafter referred to as "precursor sensor material(s)", "chemical sensor materials", "precursor molecule(s)" or "sensor molecule(s)" will react with both electrophilic (chemical species, toxins) and nucleophilic species (amino acids, peptides, proteins and other biological molecules) to form highly fluorescent compounds and thus, can be used to detect very low concentrations of hazardous chemical and biological materials and especially chemical and biological warfare agents.

Accordingly, the invention is directed, inter alia, to a "real time" method for detecting the presence of chemical and biological warfare agents by employing tunable, precursor sensor materials that mimic the physiological interaction of these agents to form highly florescent berberine-type alkaloids that can be easily and rapidly detected. For more general applications these novel precursor sensor materials can be tuned for reaction with both electrophilic and nucleophilic species. It is postulated that the molecules that constitute the chemical sensor materials react with a target species to transform two out-of-plane, weakly conjugated, short-wavelength sensor molecules into one rigid, planar, conjugated, chromophore with strong long wavelength fluorescence (53.0-560 nm) and large Stokes shift (100-180 nm). Fluorescence intensity, reactivity, wavelength, and Stokes shift can all be tuned through altering the substituents on the chemical sensor molecule.

Synthetic methodology and proof-of-principle have been demonstrated with representative electrophilic and nucleophilic chemical species.

DETAILED DESCRIPTION OF THE INVENTION

The method of the invention and materials described herein can be configured to detect an analyte, that can be an electrophilic or nucleophilic material, in a liquid or a vapor. The invention operates generally by monitoring the optical properties of a precursor material that is transformed into a rigid, planar, conjugated, chromophore with strong long wavelength fluorescence (530-560 nm) and large Stokes shift (100-180 nm) by reaction with the analyte.

In this invention advantage is taken of the well-characterized optical properties of berberine-type alkaloids, namely, high fluorescence intensity and large Stokes shifts (Pavelka, S.; Smekal, E. *Collection Czech. Chem. Commun.*, 41, 3175-69, 1976.), to detect both electrophilic and nucleophilic species generally and, in particular, chemical and biological warfare agents, hereinafter referred to by the acronym (CWA). By employing a tunable, precursor sensor material that mimics the physiological interaction of a CWA to produce a highly florescent berberine alkaloid reaction product, the CWA can be easily and rapidly detected by spectroscopic means. The term "tuneable" as employed herein means changing the character and/or position of various functionalities, such as, for example, methylene dioxy and methoxy groups, on the precursor sensor molecule, thereby affecting the fluorescence intensity and/or wavelength of the fluorescence emission and magnitude of the Stokes shift. A more complete listing of the structural and fluorescent property variations that can result from the incorporation of various functionalities can be found in Pavella (ibid.).

For the purpose of describing this invention the novel precursor sensor material can be represented by generic formula (I)

wherein, R represents a functionality or group that will react with biological or chemical warfare materials and can be thio-, hydroxy-, a protected ether including t-butyldimethyl-ether, or the isourea of carbonyldiimidizole. Fluorescence intensity, wavelength and Stokes shift of the berberine alkaloid reaction product can be tuned by altering the composition and position of the substituents on rings A and D (cf. formula 1). A preferred substituent on. rings A and D is methyoxy and a particularly preferred substituent is methylene dioxy (as shown) as well as combinations thereof.

It is believed that where the functionality R is an alcohol the interaction between the functionalized precursor molecule and a CWA can be represented by the general reaction scheme below to form the fluorescent molecule pseudocoptisine.

Pseudocoptisine,
Fluorescence @ 556 nm
Stokes Shift: 176 nm

Figure 1:
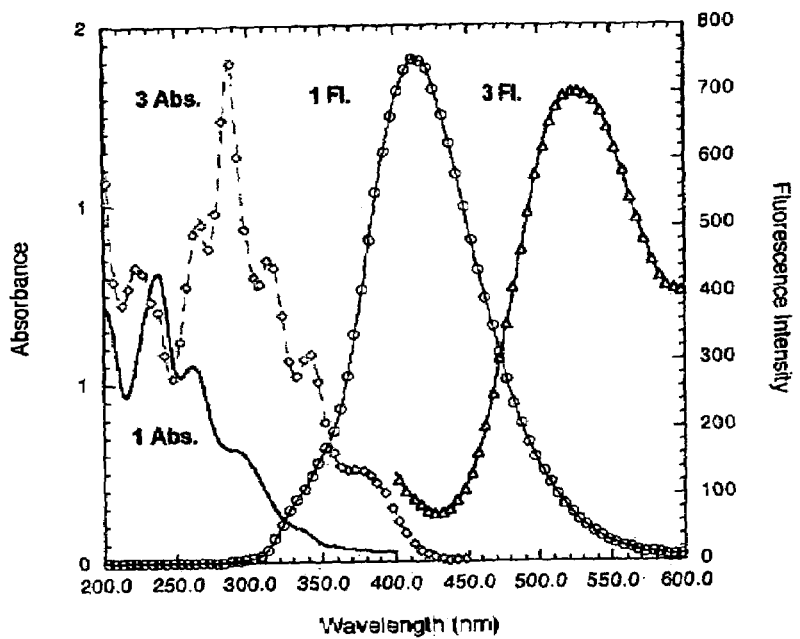
FIG. 1 shows the absorbance (Abs.) and fluorescence (Fl.) spectra of a precursor alcohol (1) and the reaction product pseudocoptisine (3).

In this proposed reaction scheme, once the precursor alcohol 1 reacts with a CWA an intermediate 2 is formed. This step is immediately followed by an intermolecular cyclization reaction resulting in a rigid planar, conjugated, highly delocalized chromophore 3, pseudocoptisine. As shown in FIG. 1, reaction product 3 has a Stokes shift of 176 nm and is highly fluorescent thereby allowing for unambiguous detection of a CWA.

It is recognized that for nucleophilic reactions and detection of bio-molecules, precursor molecule 1 can require activation of the alcohol functionality. Thus, in another aspect of the invention, a preliminary preparation step can be necessary for the detection of biological warfare agents. One preparation method can be the reaction of precursor sensor alcohol molecule 1 with carbonyldiimidizole (CDI), which is a known cross-linker for cross-linking biological molecules (proteins, antibodies and DNA) and modifying polymeric substrates such as poly(vinyl alcohol). Dicyclohexylcarbodiimide (DCC) can also be used in a similar fashion for the activation of precursor molecule 1. This process and the proposed. subsequent reaction with a protein molecule is represented by the reaction scheme below in which activation is by the use of DCC.

Here, alcohol 1 is reacted with DCC to form O-alkyl isourea 1a. It is the intermediate isourea 1a that when exposed to a biomolecule containing carboxylic acid functionalities cyclizes to form rigid planar, conjugated, highly delocalized chromophore 3. Reaction of 1a with the carboxylic acid functionality of a protein will result in the formation of molecule 1b and dicyclohexyl urea. Intramolecular ring closing of 1b forms a highly fluorescent reaction product pseudocoptisine 3.

Synthetic methodology for exemplary precursor sensor molecules 6,7-methylene-3-(3,4-methylenedioxy-6-vinylphenyl-isoquinoline and 6,7-methylene-3-(3,4-methylenedioxy-6-phenylethanol)-isoquinoline is presented in the examples below.

EXAMPLE 1

Synthesis of 6,7-Methylenedioxy-3-(3,4-methylene-dioxy-6-vinylphenyl)-isoquinoline To a solution of 1,2-methylenedioxy-5-alkynyl-6-vinyl-benzene in triethylamine (15 mL) was added Pd(PPh$_3$)$_2$Cl$_2$ (1.8.5 mg, 0.26 mmol) and CuI (2.3 mg, 0.12 mmol) and the reaction was stirred under Ar for 15 minutes. N-(4-iodobenzof[1,3]dioxol-6-yl)methylene)-tert-butylamine was added and the reaction stirred at 50 C under Ar until TLC (SiO$_2$, 1/4 ethyl acetate-petroleum ether) showed consumption of starting material. The reaction was filtered, the filtrate washed with diethyl ether (20 mL), and concentrated in vacuo. The crude imine-alkyne was used without further purification or analysis. The residue was dissolved in CHCl$_3$, AgNO$_3$ (13.8 mg, 0.81 mmol) was added, and the reaction was heated and stirred under Ar at 50 C until TLC (SiO$_2$, 1/4 ethyl acetate-petroleum ether) showed consumption of starting material. The reaction was diluted with CHCl$_3$ and washed with brine. The organic layer was removed and the aqueous layer was extracted with CHCl$_3$, the organic layers combined, dried, and concentrated in vacuo. Column chromatography (SiO2, 30/70 ethyl acetate-petroleum ether) of the residue yielded 6,7-methylene-3-(3,4-methylenedioxy-6-vinylphenyl)-isoquinoline in 26% yield as a yellow oil. $^1$H NMR (500 MHz, CDCl$_3$) δ 9.08 (s, 1H), 7.63 (s, 1H), 7.41 (s, 1H), 7.26 (s, 1H), 7.20 (s, 1H), 7.04 (s, 1H), 6.87 (dd, J=15.0, 10.0 Hz, 1H), 6.20 (s, 2H), 6.06 (s, 2H), 5.66 (dd, J=15.0, 1.0 Hz, 1H), 5.08 (dd, J=10.0, 1.0 Hz, 1H).

EXAMPLE 2

Synthesis of 6,7-methylenedioxy-3-(3,4-methylene-dioxy-6-phenylethanol)-isoquinoline To a solution of 6,7-methylenedioxy-3-(3,4-methylenedioxy-6-vinylphenyl)-isoquinoline (750 mg, 2.35 mmol) in anhydrous THF was added 1.0 M BH$_3$-THF (4.70 mL, 4.70 mmol). The reaction stirred at RT for 1 hour under Ar after which water (230 mL) was added dropwise followed by 3N NaOH (320 mL). Hydrogen peroxide (37%, 320 mL) was added dropwise and the reaction stirred for 1 hour at room temperature. Ethyl acetate (150 mL) was added to the reaction mixture, which was then washed with water (100 mL) and brine (100 mL). The organic layer was dried (MgSO$_4$) and the solvent removed in vacuo. Column chromatography (SiO$_2$, 70/30 ethyl acetate-petroleum ether) yielded 1 in 36% yield as a colorless solid. $^1$H NMR (500 MHz, CDC4$_3$) δ 9.08 (s, 1H), 7.63 (s, 1H), 7.22 (s, 1H), 7.10 (s, 1H), 6.85 (s, 1H), 6.12 (s, 2H), 5.98 (s, 2H), 3.97 (t, J=6.0 Hz, 2H), 5.08 (t, J=6.0 Hz, 2H). $^{13}$C NMR (125 MHz, CDCl$_3$) δ 151.91, 150.95, 148.82, 148.24, 147.71, 146.16, 135.76, 133.04, 132.75, 124.38, 120.48, 110.09, 109.96, 103.18, 102.61, 101.89, 101.25, 63.79, 35.29.

In order to better understand and appreciate its nature and scope, the present invention now will be described more fully hereinafter by way of various examples illustrative of the invention. This invention may, however, be embodied in many different forms and should not be construed as limited to the embodiments set forth herein but as defined by the appended claims.

EXAMPLE A

Figure 2:
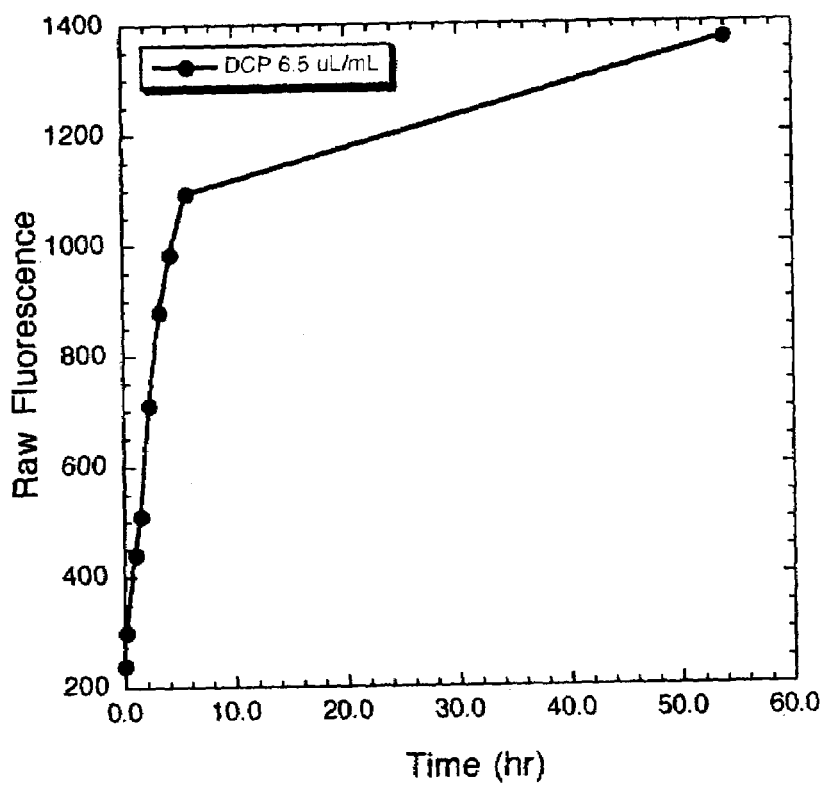
FIG. 2 shows raw fluorescence data for a precursor alcohol reacting with DCC.

A solution of alcohol 1, i.e., 6,7-methylene-3-(3,4-methylenedioxy-6-phenylethanol)-isoquinoline, was dissolved in DMSO to a 10$^{-5}$ M-solution. About 20 µL of the chemical nerve agent simulant diisopropyl chlorophosphate (DCP) was added to about 3 mL of the alcohol solution. The reaction was monitored using a Barnstead International Turner Quantech Digital filter fluorometer incorporating a narrow band excitation filter at 360 nm and a 515 nm excitation filter. The Turner spectrometer was operated in a raw fluorescence mode. The fluorescence response/time data are shown in FIG. 2.

EXAMPLE B

Figure 3:
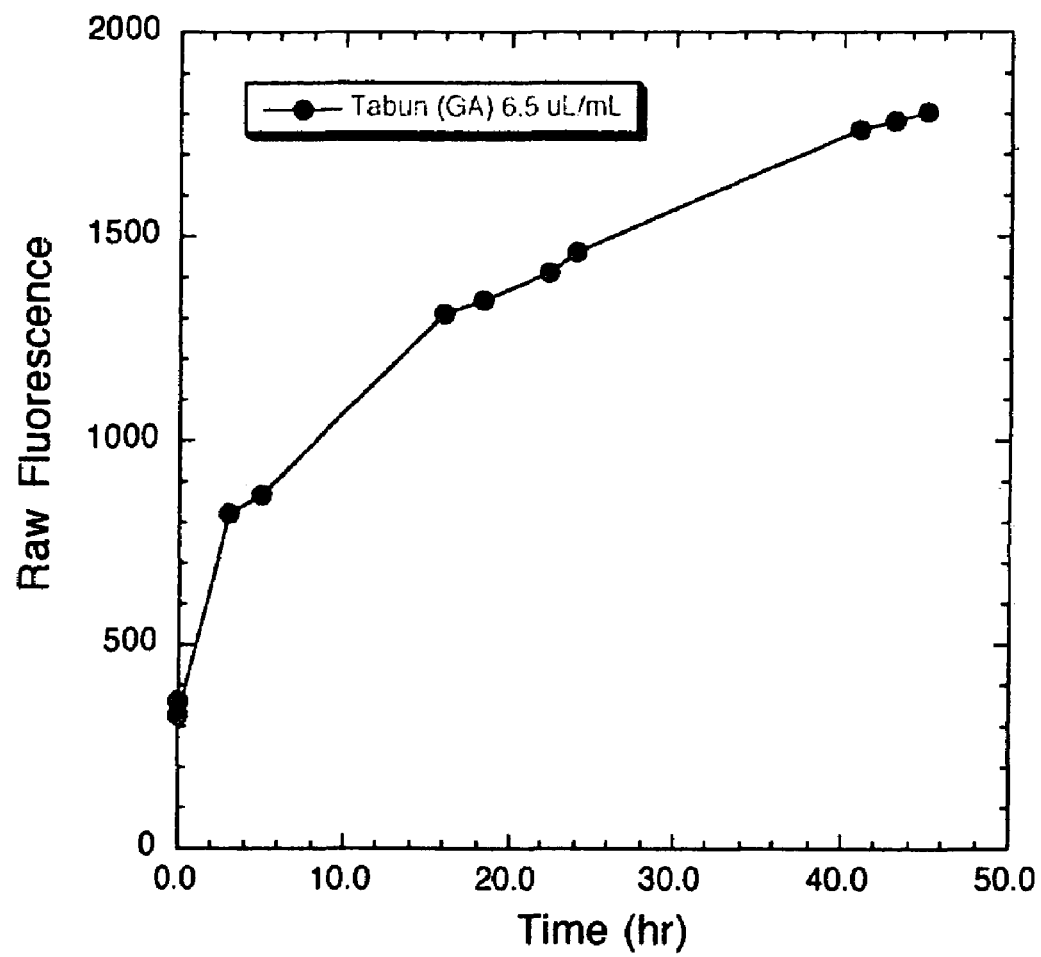
FIG. 3 shows the fluorescence data for an alcohol reacting with the nerve agent tabun.

Solutions of nerve agent tabun (Edgewood Chemical and Biological Center) were prepared by adding 20 uL of neat agent to samples containing the chemical sensor 3 mL of 6,7-methylene-3-(3,4-methylenedioxy-6-phenylethanol)-isoquinoline (1.1×10$^{-4}$ M). The reaction was monitored as in EXAMPLE A above. The Turner spectrometer was operated in raw fluorescence mode. The fluorescence response with time for reaction of the chemical sensor with tabun to form the reaction product pseudocoptisine is shown in FIG. 3.

EXAMPLE C

Alcohol 1 (5 mg), i.e., 6,7-methylene-3-(3,4-methylenedioxy-6-phenylethanol)-isoquinoline, was dissolved in deuterated CH2C12. CuCl (1 mg) and DCC (15 mg) i.e dicylcohexylcarbodimide, was added and the reaction was monitored by $^1$H NMR until complete. The solution was filtered, concentrated to dryness, dissolved in deuterated DMSO, and divided into two portions. The portions were then reacted with representative amino acids that are found in proteins. The first portion was reacted with aspartic acid (5 mg) and the second portion was reacted with lysine (5 mg). $^1$H NMR revealed that each portion rapidly reacted with the amino acids to form psuedocoptisine 3 and exhibited the same spectral properties given in FIG. 2.

It is contemplated that the instant invention can be used in numerous applications by bonding or otherwise attaching the precursor chemical material to a surface or substrate. Tethering of the chemical sensor material to a substrate can be by means of substituents such as alcohols, thiols and/or polymerizable groups such as alkenes on rings A and D of the chemical sensor (cf. formula 1).

In one embodiment of the invention the substrate can be a clear amorphous polymer that would allow detection of a CWA or other chemical species in fluid samples such as sewage or industrial discharges.

In still another embodiment, the precursor chemical sensor materials can be incorporated into a fiber optic system having a flexible fiber optic probe such as described in U.S. Pat. No. 6,623,973 to Levitsky.

In yet another embodiment of the invention, the precursor chemical sensor materials disclosed herein can be incorporated into a hand-held platform for field detection of CWA or biomolecules such as disclosed in U.S. patent application Ser. No. 10/633,871, filed Aug. 4, 2003, incorporated herein in its entirety.

We claim:

1. A precursor sensor molecule having the generic formula:

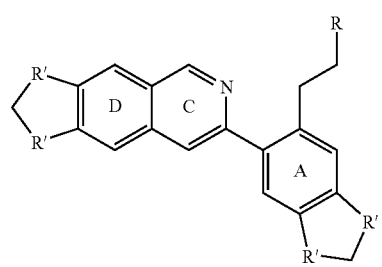

wherein, R is thio-, hydroxy-, a protected ether or carbonyl-diimidizole and R' is methylene dioxy.

* * * * *